United States Patent [19]
McClure et al.

[11] Patent Number: 5,910,834
[45] Date of Patent: *Jun. 8, 1999

[54] COLOR ON COLOR VISUAL FIELD TESTING METHOD AND APPARATUS

[75] Inventors: Richard J. McClure, San Diego; R. Kemp Massengill, Poway, both of Calif.

[73] Assignee: Virtual-Eye.Com, Inc., Leucadia, Calif.

[*] Notice: This patent is subject to a terminal disclaimer.

[21] Appl. No.: 08/936,079

[22] Filed: Sep. 23, 1997

Related U.S. Application Data

[63] Continuation-in-part of application No. 08/864,331, May 28, 1997, which is a continuation of application No. 08/700,754, Jul. 31, 1996, Pat. No. 5,864,384.

[51] Int. Cl.⁶ ........................................... A61B 3/02
[52] U.S. Cl. ................................................... 351/224
[58] Field of Search ...................... 351/205, 222, 351/223, 224, 226, 227, 237, 239, 246

[56] References Cited

U.S. PATENT DOCUMENTS

| | | | |
|---|---|---|---|
| 3,983,474 | 9/1976 | Kuipers | 324/43 |
| 4,205,224 | 5/1980 | Mecklenborg | 250/201 |
| 4,634,243 | 1/1987 | Massof et al. | 351/243 |
| 4,848,898 | 7/1989 | Massof | 351/242 |
| 4,896,962 | 1/1990 | Menn et al. | 356/152 |
| 4,897,511 | 1/1990 | Itaya et al. | 128/18 |
| 4,956,794 | 9/1990 | Zeevi et al. | 364/559 |
| 5,035,500 | 7/1991 | Rorabaugh et al. | 351/226 |
| 5,113,177 | 5/1992 | Cohen | 340/705 |
| 5,151,722 | 9/1992 | Massof et al. | 351/158 |
| 5,231,430 | 7/1993 | Kohayakawa et al. | 351/243 |
| 5,237,351 | 8/1993 | Kohayakawa et al. | 351/243 |
| 5,308,246 | 5/1994 | Balocco | 434/236 |
| 5,381,195 | 1/1995 | Rootzen et al. | 351/222 |
| 5,384,580 | 1/1995 | Kadota | 345/145 |
| 5,386,216 | 1/1995 | Iino | 345/7 |
| 5,394,517 | 2/1995 | Kalawsky | 395/129 |
| 5,398,039 | 3/1995 | Furuya et al. | 345/7 |
| 5,400,155 | 3/1995 | Ueda et al. | 359/9 |

(List continued on next page.)

FOREIGN PATENT DOCUMENTS

| | | |
|---|---|---|
| 0 428 604 | 5/1991 | European Pat. Off. . |
| 96/14793 | 5/1996 | WIPO . |

OTHER PUBLICATIONS

Andre A.; Visual Scanning in the Functional Visual Field; SID International Symposium Digest of Technical Papers; 1993; pp. 114–117.

Arditi, A.; Visualization of 2–D and 3–D Aspects of Human Binocular Vision; SID International Symposium Digest of Technical Papers; 1992; pp. 643–646.

Arnst, C.; Eyeing Glaucoma in Virtual Reality; Business Week; Jun., 1997; p. 92.

Ayache, N.; Steps Toward the Automatic Interpretation of 3D Images; 3D Imaging in Medicine: Algorithms, Systems, Applications; 1990; pp. 107–120.

(List continued on next page.)

Primary Examiner—George Manuel
Attorney, Agent, or Firm—Gerald W. Spinks

[57] ABSTRACT

A method and apparatus are disclosed for using virtual reality to present a test stimulus of a first color superimposed on a background of a second color, for testing and quantifying visual information from the eye, the visual pathways, and the brain. Headgear configuration allows the patient to observe a field of view into which sequenced test stimuli are presented by an excitation device commanded by a computer. Interactive sensory feedback both to and from the patient enables computer-driven presentation and modulation of test stimuli to measure with precision such parameters as visual field performance, visual acuity, and color vision. Using the system allows the patient unprecedented freedom of movement of the head and body, thus minimizing or even eliminating the stress and fatigue common with conventional non-virtual reality visual field testing systems.

15 Claims, 1 Drawing Sheet

U.S. PATENT DOCUMENTS

| | | | |
|---|---|---|---|
| 5,414,439 | 5/1995 | Groves et al. | 345/7 |
| 5,442,456 | 8/1995 | Hansen | 358/342 |
| 5,461,436 | 10/1995 | Campbell | 351/242 |
| 5,478,239 | 12/1995 | Fuerst et al. | 434/247 |
| 5,483,305 | 1/1996 | Kohayakawa | 351/243 |
| 5,488,508 | 1/1996 | Haseltine | 359/362 |
| 5,550,602 | 8/1996 | Braeuning | 351/243 |
| 5,565,949 | 10/1996 | Kasha, Jr. | 351/224 |
| 5,598,235 | 1/1997 | Heijl et al. | 351/224 |

OTHER PUBLICATIONS

Bancroft, G.; Tools for 3d Scientific Visualization in Computational Aerodaynamics at NASA Ames Research Center; Proceedings of the SPIE: 1989; pp. 161–172.

Barfield, W.; Spatial Situational Awareness as a Function of Frame of Reference, Virtual Eyepoint Elevation, and Geometric Field of View; SID International Symposium Digest of Technical Papers; 1993; pp. 107–110.

Benedikt, M.; Cyberspace, Some Proposals; Cyberspace, First Steps; 1991; pp. 1232–168.

Bertol, D.; Architecture of Images, An Investigation of Architectural Representations and the Visual Perception of Three–Dimensional Space; Leonardo, vol. 29, No. 2; 1996; pp. 87–94.

Bethke, W.; Glaucoma Screening to Go; Review of Ophthalmology; Jul., 1997; p. 21.

Bricken, M.; *Virtual Worlds: No Interface to Design;* Cyberspace, First Steps; 1991; pp. 363–368.

Carlson, A.; Development of a Binocular Visor Projection Helmet–Mounted Display; SID International Symposium Digest of Technical Papers; 1993; pp. 131–134.

Dickinson, R.; A Unified Approach to the Design of Visualization Software for the Analysis of Field Problems; Proceedings of the SPIE; 1989; pp. 173–180.

Dickinson, R.; Interactive 4–D Visualization of Fields; Computer Science Technical Report; 1989; pp. 1–10.

Dickinson, R.; A Unified Approach to Interface Design for Data Visualization Using Desktop and Immersion Virtual Environments; Virtual Reality Applications; 1995; pp. 309–320.

Eddings, J.; *How Virtual Reality Works;* Ziff–Davis Press; 1994; pp. 19–32, 40–45, 53–55, 63, 65–67, 69–70, 72–73, 76–78, 84–90, 98–103, 120–122, 124–125, 146–149.

Fuchs, H.; Systems for Display of Three–Dimensional Medical Image Data; 3D Imaging in Medicine: Algorithms, Systems, Applications; 1990; pp. 315–331.

Gilboa, P.; Designing the Right Visor; Proceedings of the SPIE; 1991; pp. 154–163.

Granieri, J.; Stimulating Humans in Virtual Reality; Virtual Reality Applications; 1995; pp. 265–268.

Grunwald, A.; Visual Field Information in the Nap–of–the–Earth Flight Teleoperated Helmet–Mounted Displays; Proceedings of the SPIE; 1991; pp. 132–153.

Harrington, D.; Normal Visual Field; The Visual Fields: A Textbook and Atlas of Clinical Perimetry; 1976; pp. 97–104.

Harrington, D.; Normal Visual Field; Abnormal Visual Fields: A Textbook and Atlas of Clinical Perimetry; 1976; pp. 107–147.

Hendrix, C.; Presence within Virtual Environments as a Function of Visual Display Parameters; Presence, vol. 5, No. 3; 1996; pp. 274–289.

Jaa–Aro, K.; An Overview of Virtual Reality Research in the Nordic Countries; The Virtual Reality Casebook; 1994; pp. 138–167.

Jacobsen, R.; Designing in Virtual Space; The Virtual Reality Casebook; 1994; pp. 243–249.

Kalawsky, R.; *The Science of Virtual Reality of Virtual Environments;* Addison–Wesley Publishing; 1993; pp. 1–16, 24–33, 43–69, 107–188, 210–220, 256–277, 315–319, 344, 347–355.

Kaufman, A.; Direct Interaction with a 3–D Volumetric Environment; Proceedings SIGGRAPH; 1990; pp. 33–34.

Kollin, J.; A Retinal Display for Virtual–Environment Applications; SID International Symposium Digest of Technical Papers; 1993; p. 827.

Leigh, J.; Virtual Reality in Computational Neuroscience; Virtual Reality Applications; 1995; pp. 293–294, 300–304.

Loeffler, C.; What Is Virtual Reality?; The Virtual Reality Casebook; 1994; pp. xiii–xxv.

Massof, R.; Low Vision Enhancement System; Johns Hopkins APL Technical Digest; 1994; pp. 120–124.

Massof, R.; Low Vision Enhancement; Vision for the Future; Eyecare Technology; 1994; pp. 32–35.

Penny, S.; Virtual Reality as the Completion of the Enlightenment; The Virtual Reality Casebook; 1994; pp. 199–200.

Peters, D.; Chasing the Eye: *An Eye–Tracked Display for the Stimulation Industry—The How and the Why;* 1991; pp. 495–497.

Pimentel, K.; *Virtual Reality Through the New Looking Glass;* Intel/McGraw–Hill; 1995; pp. xxi, 5–6, 8–12, 19–22; 65–71, 80–87, 94–106, 148–167, 201–202, 241–244, 279–299, 359–370, 417.

Regan, E.; Some Human Factors Issues in Immerse Virtual Reality: Fact and Speculation; Virtual Reality Applications; 1995; pp. 163–164.

Rheingold, H.; *Virtual Reality;* Touchstone/Simon & Schuster; 1991; pp. 113, 131–154, 215–255.

Satava, R.; Virtual Reality for the Physician of the 21st Century; Virtual Reality Applications; 1995; pp. 19–26.

Sperlich, T.; We Continue Searching: Virtual Reality Research in Germany; The Virtual Reality Casebook; 1994; pp. 152–167.

Stone, A.; Will the Real Body Please Stand Up?: Boundary Stories about Virtual Culutures; Cyberspace: First Steps; 1991; pp. 95–99.

Stuart, R.; The Design of Virtual Environments; McGraw–Hill; 1996; pp. 10, 13, 17–30, 45–47, 53–55, 60–61, 103–104, 114–117, 133–143.

Thalmann, D.; Applications of Virtual Humans in Virtual Reality; Virtual Reality Applications; 1995; pp. 271–274.

Traub, D.; The Promise of Virtual Reality for Learning; The Virtual Reality Casebook; 1994; pp. 107–117.

Wann, J.; Natural Problems for Stereoscopic Depth Perception in Virtual Environments; Vision Research; 1995; pp. 2731–2736.

Webster, J.; Stereoscopic Full Field of Vision Display System to Produce Total Visual Telepresence; Proceedings of the SPIE; 1989; pp. 63–70.

Welch Allyn advertisement; Review of Ophthalmology; Jul., 1997; 4 un–numbered pages.

Wexelblat, A.; Giving Meaning to Place: Semantic Spaces; Cyberspace: First Steps; 1991; pp. 257–271.

Wodaski, R.; Virtual Reality Madness!1996; Sams Publishing; 1995; pp. 216–229, 588–590.

Yamaguchi, H.; Proposal for a Large Visual Field Display Employing Eye Movement Tracking; Proceedings of the SPIE; 1989; pp. 13–20.

Adams, A.; Spectral sensitivity and color discrimination changes in glaucoma and glaucoma–suspect patients; Invest. Ophthalmol. & Vis. Sci. vol. 23; Oct. 1982; pp. 516–524.

Adams, A.; Clinical Measures of Central Vision Function in Glaucoma and Ocular Hypertension; Arch. Ophthalmol. vol. 105; Jun. 1987; pp. 782–787.

Airaksinen, P.; Color Vision and Retinal Nerve Fiber Layer in Early Glaucoma; American Journal of Ophthalmol. vol. 101; Feb. 1986; pp. 208–213.

Breton, M.; Age Covariance Between 100–Hue Color Scores and Quantitative Perimetry in Primary Open Angle Glaucoma; Arch. Opthalmol. vol. 105; May 1987; pp. 642–645.

Caprioli, J.; Early Diagnosis of Functional Damage in Patients With Glaucoma; Arch. Ophthalmol. vol. 115; Jan. 1997; pp. 113–114.

Drance, S.; Acquired Color Vision Changes in Glaucoma; Arch. Ophthalmol. vol. 99; May 1981; pp. 829–831.

Falcao–Reis, F.; Macular colour contract sensitivity in ocular hypertension and glaucoma: evidence for two types of defect; British Journal. of Ophthalmol. vol. 75; 1991; pp. 598–602.

Felius, J.; Functional Characteristics of Blue–on–Yellow Perimetric Thresholds in Glaucoma; Invest. Ophthalmol. & Vis. Sci. vol. 36; Jul. 1995; pp. 1665–1674.

Flammer, J.; Correlation Between Color Vision Scores and Quantitative Perimetry in Suspected Glaucoma; Arch. Ophthalmol. vol. 102; Jan. 1984; pp. 38–39.

Gunduz, K.; Color Vision Defects in Ocular Hypertension and Glaucoma; Arch. Ophthalmol. vol. 106; Jul. 1988; pp. 929–935.

Hamill, T.; Correlation of Color Vision Deficits and Observable Changes in the Optic Disc in a Population of Ocular Hypertensives; Arch. Ophthalmol. vol. 102; Nov. 1984; pp. 1637–1639.

Hart, W.; Color Contrast Perimetry; Invest. Ophthalmol. & Vis. Sci. vol. 25; Apr. 1984; pp. 400–413.

Hart, W.; Color Perimetry of Glaucomatous Visual Field Defects; Ophthalmol. vol. 91; Apr. 1984; pp. 338–346.

Hart, W.; Color Contract Perimetry: The Spatial Distribution of Color Defects in Optic Nerve and Retinal Diseases; Ophthalmol. vol. 92; Jun. 1985; pp. 768–776.

Hart, W.; Glaucomatous Visual Field Damage; Invest. Ophthalmol. & Vis. Sci. vol. 31; Feb. 1990; pp. 359–367.

Heron, G.; *Central Visual Fields For Short Wavelength Sensitive Pathways in Glaucoma and Ocular Hypertension;* Invest. Ophthalmol. & Vis. Sci. vol. 29, Jan. 1988; pp. 64–72.

Humphrey Instruments: Humphrey Field Analyzer II; Advertising Flyer, in use for general public. Copyright, 1996.

Interzeag AG; Blue/Yellow perimetry; Product Announcement; Ocular Surgery News vol. 15; Jun. 1997.

Interzeag AG; Clairvoyant Octopus: Octopus Blue/Yellow predicts defects further into the future than any competing product: Product Advertisement; Ocular Surgery News vol. 15; Jul. 1997.

Johnson, C.; Blue–on–Yellow Perimetry Can Predict the Development of Glaucomatous Visual Field Loss; Arch. Ophthalmol. vol. 111; May 1993; pp. 645–650.

Johnson, C.; Progression of Early Glaucomatous Visual Field Loss as Detected by Blue–on–Yellow and Standard White Automated Perimetry; White–on–White Automated Perimetry; Arch. Ophthalmol. vol. 111; pp. 651–656.

Johnson, C.; Short–Wavelength Automated Perimetry in Low–, Medium–, and High–Risk Ocular Hypertensive Eyes: Arch. Ophthalmol. vol. 113; Jan. 1995; pp. 70–76.

Lewis, R.; Automated perimetry and short wavelength sensitivity in patients with asymmetric intraocular pressures; Graefe's Arch. Clin. Exp. Ophthalmol. vol. 231; 1993; pp. 274–278.

Logan, N.; Detecting Early Glaucomatous Visual Field Changes With a Blue Stimulus; American Journal of Ophthalmol. vol. 95; Apr. 1983; pp. 432–434.

Mindel, J.; Visual Field Testing With Red Targets; Arch. Ophthalmol. vol. 101; Jun. 1983; pp. 927–929.

Moss, I.; The Influence of Age–Related Cataract on Blue–on–Yellow Perimetry; Invest. Ophthalmol. & Vis. Sci. vol. 36; Apr. 1995; pp. 764–773.

Motolko, M.; The Early Psychophysical Disturbances in Chronic Open–angle Glaucoma; Arch. Ophthalmol. vol. 100; Oct. 1982; pp. 1632–1634.

Quigley, H.; Chronic Glaucoma Selectively Damages Large Optic Nerve Fibers; Invest. Ophthalmol. & Vis. Sci. vol. 28; Jun. 1987; pp. 913–920.

Sample, P.; Isolating the Color Vision Loss in Primary Open–Angle Glaucoma; American Journal of Ophthalmol. vol. 106; Dec. 1988; pp. 686–691.

Sample, P.; Color Perimetry for Assessment of Primary Open–Angle Glaucoma; Invest. Ophthalmol. & Vis. Sci. vol. 31; Sep. 1990; pp. 1869–1875.

Sample, P.; Report; Progressive Color Visual Field Loss in Glaucoma; Invest. Ophthalmol. & Vis. Sci. vol. 33; May 1992; pp. 2068–2071.

Sample, P.; Short–wavelength Color Visual Fields in Glaucoma Suspects at Risk: American Journal of Ophthalmol. vol. 115; Feb. 1993; pp. 225–233.

Sample, P.; Short–wavelength Automated Perimetry Without Lens Density Testing; American Journal of Ophthalmol. vol. 118; Nov. 1994; pp. 632–641.

Wild, J.; The Statistical Interpretation of Blue–on–Yellow Visual Field Loss; Invest. Ophthalmol. & Vis. Sci. vol. 36; Jun. 1995; pp. 1398–1410.

Yamazaki, Y.; Correlation Between Color Vision and Highest Intraocular Pressure in Glaucoma Patients; American Journal of Ophthalmol. 106; Oct. 1988; pp. 397–399.

Yamazaki, Y.; A Comparison of the Blue Color Mechanism in High– and Low–tension Glaucoma; Ophthalmol. vol. 96; Jan. 1989; pp. 12–15.

Yu, T.; Peripheral Color Contrast; Invest. Ophthalmol. & Vis. Sci. vol. 21; Sep. 1991; pp. 2779–2789.

Abelson, M.; Glaucoma Management; Review of Ophthalmology; Oct., 1996; pp. 160–161.

American Academy of Ophthalmology; *Final Program, Centennial Meeting;* Oct., 1996; pp. 192–193.

COLOR ON COLOR VISUAL FIELD TESTING METHOD AND APPARATUS

CROSS REFERENCE TO RELATED APPLICATIONS

This is a continuation-in-part patent application of co-pending U.S. patent application Ser. No. 08/864,331, filed on May 28, 1997, and entitled "Visual Field Testing Method and Apparatus", which is a continuation patent application of co-pending U.S. patent application Ser. No. 08/700,754, filed on Jul. 31, 1996, now U.S. Pat. No. 5,864,384 and entitled "Visual Field Testing Method and Apparatus Using Virtual Reality".

FEDERALLY SPONSORED RESEARCH OR DEVELOPMENT

Not Applicable

BACKGROUND OF THE INVENTION

This invention relates to optical testing of the eye's sensitivity to various parameters of light, and in particular to visual field evaluation, using a virtual reality system.

In the field of medicine where disorders of the eye are treated, it is necessary to measure the sensitivity to light in various regions of the light-sensitive retina. So doing measures function, as well as quantifying disorders of the eye and the retina, the optic nerve, the optic chiasm, the visual pathways to the brain, and the brain itself Visual field testing is mandatory for glaucoma diagnosis and treatment. Apparatus to measure the field of vision is used by ophthalmologists and optometrists for these purposes and is relatively complex in its various functions, some of which complexity tends to make the human patient become tired or lose attention to the test.

BRIEF SUMMARY OF THE INVENTION

The purpose of the presently-described method and apparatus for visual field testing is to allow the sensitivity of the visual field to be measured without the attendant stress of the patient, while preserving accuracy, and while increasing the sensitivity of the test to promote early detection of defects such as glaucomatous damage. The means by which this is accomplished uses concepts and apparatus from virtual reality. Virtual reality is a term applied loosely to the experience of an individual when exposed to the appearance of surroundings which are presented by interactive apparatus for stimulation of the senses. The primary cues are usually visual, supplemented by audio, and the feedback to the apparatus is generally by physical movements of the individual experiencing the virtual reality (such as pressing a button or a switch, or speaking into a microphone).

The disclosed virtual reality visual field measuring method and apparatus uses a head-mounted goggle or face mask unit to present visual and audio stimuli to a patient. The visual portion has both relatively fixed image information, and superimposed visual areas, which may vary in time, place, color, and intensity. These stimuli are generated and controlled by software in an associated computer, which receives interactive feedback stimuli from the patient. Such stimuli include, but are not limited to, direction of gaze sensing, eyelid movement and blinking, audio, and hand pressure signals on cue. In the present invention, variation of colors in the background and in the test stimulus is emphasized.

Content of the software is dictated by the need to provide technically acceptable protocols. Such protocols provide for examining wide and narrow fields of view, selected areas, such as the blind spot or the fovea, and measurements of thresholds for sensitivity to light intensity, or, if desired, color. These are usually done for one eye at a time, each looking at the same, or similar, field of views.

Active feedback sensing alerts the system to patient loss of attention in general, or loss of fixation in particular, for notation and reiteration of test stimuli. In the presently-described method and apparatus, provision is also made for reiteration of individual test points when a result is found to be inconsistent with a predetermined norm, or when lack of concentration or poor cooperation becomes evident, with appropriate care taken to provide no leading cues which may cause false positive or false negative responses. The software allows optional restful imagery to be provided in the "background," in addition to a conventional, uniform featureless field. The imagery in various quadrants/areas may be patterns, or low-contrast images, and may move quickly or slowly, and may have intensity, color, or temporal modulation. The intensity, color, location, and duration of the superimposed test points are displayed by conventional electronic means, such as are now used in image presentations. Such means include cathode-ray tube, electroluminescent, liquid crystal, and gas discharge panels. A hard-copy printout documenting patient responses is provided for the physician's records.

The present system provides relief from the stress of being required to concentrate, without head movement, one's gaze at a fixed location, as is the case with conventional visual field testers. The gaze sensor may be multi-element, so as to allow the gaze to be detected in a small solid angular range and, within this range, the effective fixation will be deemed to be maintained. The software may include an interest-fixation icon which encourages the gaze to trace its motion within the allowed solid angle, thus avoiding fixation fatigue. The software keeps track of the location of the test point frame of reference within that solid angle of displacement, so as to provide accurate mapping of test data on the field of view presented to the retina. The presentation of a test stimulus of a first color, superimposed on a background of a second color, achieving a higher testing sensitivity than known before, is much more easily accomplished using the virtual reality apparatus of the present invention than when using other known equipment.

In addition to visual field testing, it is certainly within the scope of this invention to provide other virtual reality computer-driven, interactive testing capability, such as for visual acuity and color testing.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 2(*b*) is a schematic view of the apparatus of FIG. 1 measuring a horizontal angular field of view.

DETAILED DESCRIPTION OF THE INVENTION

Figure 1:
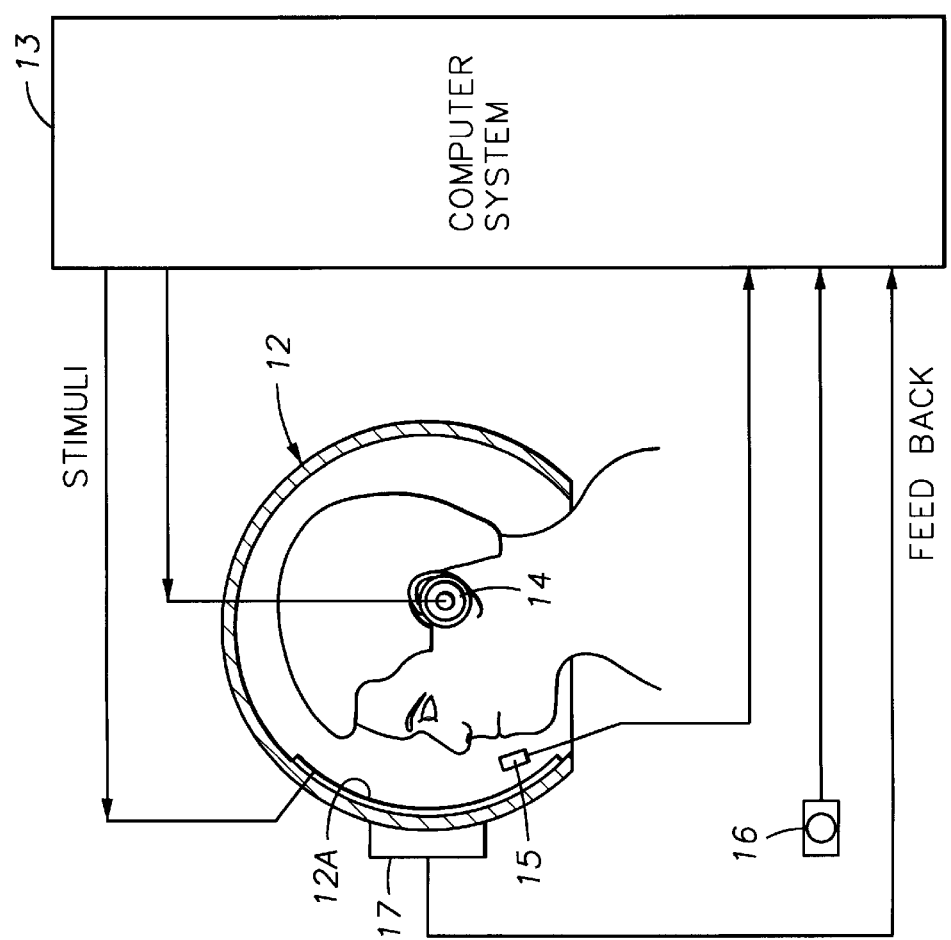
FIG. 1 is a schematic view of the apparatus of the present invention.

FIG. 1 shows a schematic of the virtual reality visual field testing system 5 of the present invention, in which a headgear assembly 12 is connected to a computer 13, which delivers a visual signal to a head-gear display screen 12(a), and an audio signal to a head-gear earphone 14.

The head-mounted visual display apparatus, head-gear 12, which remains in a fixed spatial relationship to the patient's head during testing of the visual field, is adjustable to suit the individual patient, and is mounted on the patient's head by conventional means. The screen display 12(a) is part of the head-gear 12 and encompasses the maximum field of view required. The head-gear 12 is provided with an integral microphone 15 and a speaker or earphone 14, for audio communication and feedback, and a multi-element gaze-aim sensor array 17. The microphone 15 provides feedback audio response to the computer 13. The head-gear assembly 12 is connected, by appropriate means, to the computer 13 which provides the necessary visual and audio stimuli for the patient, and which receives the feedback responses to enable interactive functioning of the system. A hand-operated switch 16 is incorporated to provide feedback to the computer 13, and the gaze sensor 17, mounted in the direction of gaze, provides optical gaze direction feedback to the computer 13.

Figure 2A:
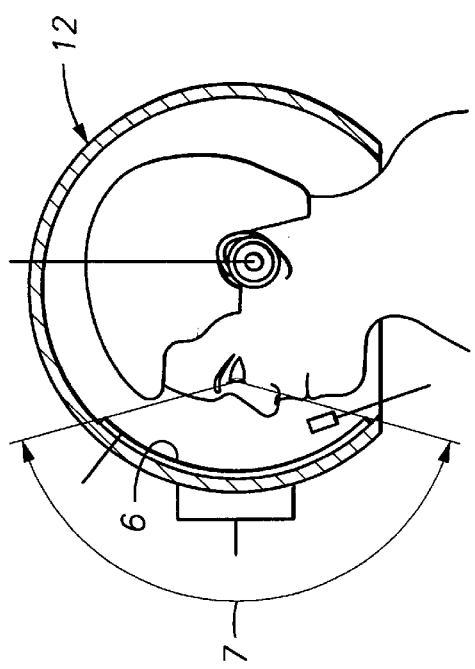
FIG. 2(*a*) is a schematic view of the apparatus of FIG. 1 measuring a vertical angular field of view.

FIG. 2(a) shows, by dashed line 6, a vertical image surface covering an angular field of view 7 on the screen display 12(a).

Figure 2B:
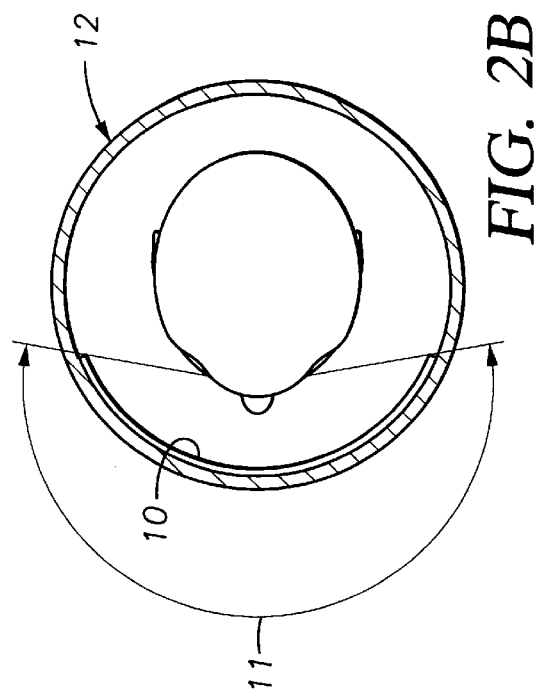

FIG. 2(b) shows, by dashed line 10, a horizontal image surface covering an angular field of view 11 on the screen display 12(a).

An element of the virtual reality visual field testing system 5 is that it allows the patient the freedom to shift his/her gaze, while in the test mode, without disruption of the process, thus relieving one of the causes of patient stress. Another feature provided is the ability to modulate the background scene brightness, contrast, color, optical stimulus size and detail, and duration of the test stimuli, all of which serve to relieve fatigue of the patient. Of paramount significance is that the patient may move around bodily, since the head gear 12 is portable and, in addition, electrical interfaces to the computer 13 may be wireless.

In addition to a vastly more patient-friendly and portable test setting, a further significant advantage of the presently-described method and apparatus is that background light intensity and other parameters can be easily calibrated to predetermined settings, thus eliminating the requirement mandated by conventional visual field testers to calibrate these parameters for the entire room. For instance, the fact that room brightness can vary almost imperceptibly, but yet significantly, from day to day in conventional visual field testing situations creates built-in unreliability of the test data received from the patient.

Furthermore, feelings of anxiety frequently displayed by patients undergoing conventional visual field testing in which first one eye and then the fellow eye is covered with an occluder patch can be eliminated in the preferred embodiment, since both eyes can be tested simultaneously, or separately and independently, through the use of individual eye goggles, or an appropriate face mask, to provide gaze separation.

Any desired imagery can be provided in the "background," or a conventional, uniform featureless field can be used. The background in various quadrants/areas may include patterns, or low-contrast images, and if present, these images may move quickly or slowly. Further, the intensity or color of the background may be changed, and any image, color, or brightness can be modulated over time. The shape, intensity, color, location, and duration of the superimposed test points also may be changed, and these characteristics can be modulated over time.

The foveal region of the retina contains a high density of cones, the color sensitive receptors, and the rest of the retina is populated mainly by rods, which are relatively insensitive to color. Therefore, the use of a test stimulus of a first color superimposed on a background of a second color is a beneficial practice to be incorporated in some visual field testing, especially in peripheral visual field testing. This practice is known to improve the sensitivity of visual field testing, resulting in earlier detection of glaucomatous damage. This advantage can be employed by using various combinations of colors. It has been determined that a particularly beneficial combination of colors is the use of a blue test stimulus on a yellow background.

In the present invention, a test stimulus of a first color, preferably blue, can be superimposed on a background of a second color, preferably yellow, either for viewing by both eyes, or for viewing by only one eye. The second eye can be presented with only a background of the second color. Presenting the color-on-color image for only one eye can be useful in preventing retinal rivalry, thereby reducing the stress imposed upon the patient during testing.

Whether viewed by one eye or both, if yellow is used for the background, it produces a relatively strong excitation of the medium wave length and long wave length retinal cone receptors, while producing little or no excitation of the short wave length retinal cone receptors. On the other hand, if blue is used for the test stimulus, it produces a relatively strong excitation of the short wave length retinal cone receptors, while producing little or no excitation of the medium wave length and long wave length retinal cone receptors.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual field testing apparatus, comprising:
    a frame, said frame being adapted to mount in a substantially motionless relationship to the head of a patient, while allowing the head to move;
    an electronic image display device mounted to said frame, said display device being constructed and positioned to display an electronic image encompassing the visual field of at least one eye of a patient wearing said frame, said image including a test stimulus, said test stimulus having its visibility enhanced by color selection;
    a gaze sensing device adapted to sense the orientation of at least one eye of a patient wearing said frame; and
    a computer, said computer being connected to said display device to generate said electronic image including said color-enhanced test stimulus, said computer being capable of receiving at least one signal and calculating at least one characteristic of the visual field of the patient.

2. A visual field testing apparatus as recited in claim 1, wherein:
    said electronic image further includes a background upon which said test stimulus is displayed;
    said test stimulus exhibits a first color; and
    said background exhibits a second color different from said first color.

3. A visual field testing apparatus as recited in claim 2, wherein said first color is blue and said second color is yellow.

4. A visual field testing apparatus as recited in claim 1, wherein said at least one signal received by said computer is a gaze orientation signal.

5. A visual field testing apparatus as recited in claim 4, wherein said computer receives a gaze orientation signal and a patient response signal.

6. A visual field testing apparatus as recited in claim 5, further comprising a response sensing device separate from said gaze sensing device;

wherein:

said gaze orientation signal is generated by said gaze sensing device; and said patient response signal is generated by said response sensing device.

7. A visual field testing apparatus as recited in claim 6, wherein said response sensing device comprises a switch manipulated by the patient.

8. A visual field testing apparatus as recited in claim 6, wherein said response sensing device comprises a motion detector.

9. A visual field testing apparatus as recited in claim 6, wherein said response sensing device comprises a sound detector.

10. A visual field testing apparatus as recited in claim 6, wherein said response sensing device comprises a gaze sensor.

11. A visual field testing apparatus, comprising:

a frame, said frame being adapted to mount in a substantially motionless relationship to the head of a patient, while allowing the head to move;

an electronic image display device mounted to said frame, said display device being constructed and positioned to display an electronic image encompassing the visual field of at least one eye of a patient wearing said frame, said image including a test stimulus of a first color displayed upon a background of a second color;

a gaze sensing device adapted to sense the orientation of at least one eye of a patient wearing said frame and to generate a gaze orientation signal;

a response sensing device adapted to sense a patient's response to a visual stimulus and to generate a response signal; and a computer, said computer being connected to said display device to generate said electronic image including said color-enhanced test stimulus, said computer being connected to said gaze sensing device to receive said gaze orientation signal, said computer being connected to said response sensing device to receive said response signal, and said computer being capable of measuring said gaze orientation signal and said response signal and calculating at least one characteristic of the visual field of the patient.

12. A visual field testing apparatus as recited in claim 11, wherein said first color is blue and said second color is yellow.

13. A method for measuring at least one characteristic of the visual field of a patient, comprising:

mounting a virtual reality apparatus in a substantially motionless relationship to the head of a patient, while allowing the head to move, said virtual reality apparatus having an electronic image display device and at least one sensing device, said virtual reality apparatus being connected to a computer;

displaying an electronic image generated by said computer, said image encompassing the visual field of at least one eye of the patient, said image including a test stimulus;

enhancing the visibility of said test stimulus by color selection;

sensing the orientation of at least one eye of the patient and generating a gaze orientation signal;

sensing the patient's response to said electronic image and generating a response signal;

receiving said gaze orientation signal and said response signal with said computer and calculating at least one characteristic of the visual field of the patient.

14. A method as recited in claim 13, further comprising:

displaying said test stimulus on a background; and enhancing said visibility of said test stimulus by displaying said test stimulus in a first color and displaying said background in a second color different from said first color.

15. A method as recited in claim 14, further comprising:

displaying said test stimulus in blue; and displaying said background in yellow.

* * * * *